United States Patent
Salituro et al.

(12)
(10) Patent No.: US 6,635,644 B2
(45) Date of Patent: Oct. 21, 2003

(54) INHIBITORS OF P38

(75) Inventors: Francesco Salituro, Marlborough, MA (US); Guy Bemis, Arlington, MA (US); Huai Gao, Natick, MA (US); Ghotas Evindar, Toronto (CA)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

(21) Appl. No.: 09/809,921

(22) Filed: Mar. 16, 2001

(65) Prior Publication Data

US 2002/0010170 A1 Jan. 24, 2002

Related U.S. Application Data

(63) Continuation-in-part of application No. PCT/US99/21567, filed on Sep. 16, 1999.
(60) Provisional application No. 60/101,013, filed on Sep. 18, 1998.

(51) Int. Cl.$^7$ ..................... C07D 487/04; A61K 31/519
(52) U.S. Cl. ........................................ 514/248; 544/236
(58) Field of Search ........................... 544/236; 514/248

(56) References Cited

FOREIGN PATENT DOCUMENTS

WO    WO 98/27098 A1    6/1998

OTHER PUBLICATIONS

Laszlo et al., Pyrroles and other Heterocycles as inhibitors of p38 Kinsase, Biorganic & Medicinal Chemistry Letters, 8(19), pp. 2689–2694, 1998.*

Layzer, Degenerative Diseases of the Nervous System, Cecil Textbook of Medicine, 20th Edition, vol. 2, pp. 2050–2057, 1996.*

Simone, Oncology: Introduction, Cecil Textbook of Medicine, 20th Edition, vol. 1, pp. 1004–1010, 1996.*

* cited by examiner

Primary Examiner—Deepak Rao
(74) Attorney, Agent, or Firm—Fish & Neave; James F. Haley, Jr.; Kristin M. Joslyn

(57) ABSTRACT

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

16 Claims, No Drawings

INHIBITORS OF P38

This application is a continuation-in-part of PCT/US99/21567, filed Sep. 16, 1999, which claims benefit of U.S. Provisional Application No. 60/101,013, filed Sep. 18, 1998.

TECHNICAL FIELD OF INVENTION

The present invention relates to inhibitors of p38, a mammalian protein kinase is involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) has been discovered. Members of this family are Ser/Thr kinases that activate their substrates by phosphorylation [B. Stein et al., *Ann. Rep. Med. Chem.*, 31, pp. 289–98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, is isolated from murine pre-B cells that are transfected with the lipopolysaccharide (LPS) receptor, CD14, and induced with LPS. p38 has since been isolated and sequenced, as has the cDNA encoding it in humans and mouse. Activation of p38 has been observed in cells stimulated by stress, such as treatment of lipopolysaccharides (LPS), UV, anisomycin, or osmotic shock, and by treatment with cytokines, such as IL-1 and TNF.

Inhibition of p38 kinase leads to a blockade in the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., *Endocrinol.*, 136, pp. 3054–61 (1995)].

Based upon this finding it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have been implicated in the area of pain management through inhibition of prostaglandin endoperoxide synthase-2 induction. Other diseases associated with Il-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and, in particular, p38. PCT publication WO 98/27098 also describes substituted nitrogen-containing heterocycles as p38 inhibitors. However, the efficacy of these inhibitors in vivo is still being investigated.

Accordingly, there is still a great need to develop other potent, p38-specific inhibitors that are useful in treating various conditions associated with p38 activation.

SUMMARY OF THE INVENTION

The present invention addresses this problem by providing compounds that demonstrate strong and specific inhibition of p38.

In one embodiment, these compounds have the general formulae:

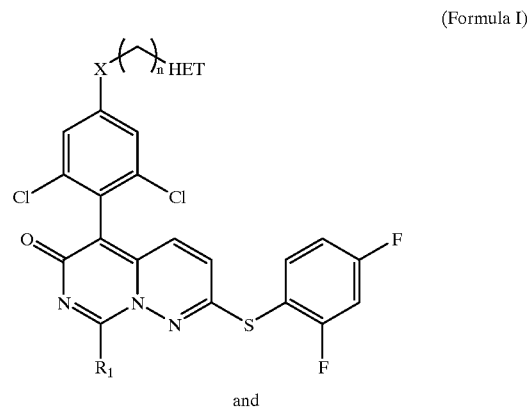

(Formula I)

and

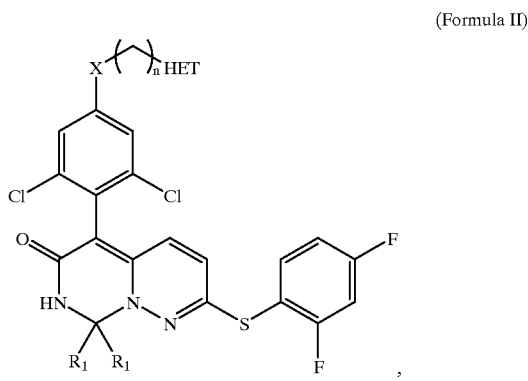

(Formula II)

pharmaceutically acceptable salts thereof.

HET is a 5–7-membered heterocycle with 1 to 4 N, S or O atoms, which heterocycle is substituted with 1 to 3 $C_1$–$C_4$ branched or straight chain alkyl groups. HET may optionally be substituted with halo, cyano, $N(R')_2$, OR', $CO_2R'$, CON$(R')_2$, and $SO_2N(R^2)_2$.

X is O or NR'.

n is 1 to 3.

R' is selected from hydrogen, ($C_1$–$C_3$)-alkyl, ($C_2$–$C_3$)-alkenyl or alkynyl, phenyl or phenyl substituted with 1 to 3 substituents independently selected from halo, methoxy, cyano, nitro, amino, hydroxy, methyl or ethyl; or a 5–6 membered heterocyclic ring system optionally substituted with 1 to 3 substituents independently selected from halo, methoxy, cyano, nitro, amino, hydroxy, methyl or ethyl.

$R_1$ is selected from hydrogen, ($C_1$–$C_3$)-alkyl, OH, or O—($C_1$–$C_3$)-alkyl.

$R^2$ is selected from hydrogen, ($C_1$–$C_3$)-alkyl, or ($C_1$–$C_3$)-alkenyl; each optionally substituted with —$N(R')_2$, —OR', SR', —C(O)—$N(R')_2$, —$S(O_2)$—$N(R')_2$, —C(O)—OR', or $R^3$.

$R^3$ is selected from 5–6 membered aromatic carbocyclic or heterocyclic ring systems.

In another embodiment, p38-inhibitory compounds have the general formula:

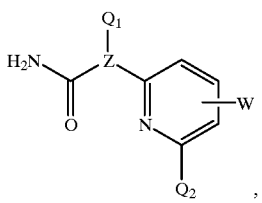

(Formula III)

acceptable salts thereof.

Each of $Q_1$ and $Q_2$ are independently selected from 5–6 membered aromatic carbocyclic or heterocyclic ring systems, or 8–10 membered bicyclic ring systems comprising aromatic carbocyclic rings, aromatic heterocyclic rings or a combination of an aromatic carbocyclic ring and an aromatic heterocyclic ring.

The rings that make up $Q_1$ are optionally substituted with 1 to 4 substituents, each of which is independently selected from J; halo; $C_1$–$C_4$ alkyl optionally substituted with $NR'_2$, OR', $CO_2R'$ or $CONR'_2$; O—$(C_1$–$C_4)$-alkyl optionally substituted with A, T—C(O)R', $OPO_3H_2$, $NR'_2$, $NR'_2$, OR', $CO_2R'$ or $CONR'_2$; $NR'_2$; $OCF_3$; $CF_3$; $NO_2$; $CO_2R'$; CONR'; SR'; $S(O_2)N(R')_2$; $SCF_3$; CN; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N=C-N(R')_2$.

The rings that make up $Q_2$ are substituted with J and optionally substituted with halo, $C_1$–$C_4$ straight chain or branched alkyl, hydroxy, methoxy, trifluoromethyl, trifluoromethoxy, cyano, or amino.

J is a $C_1$–$C_4$ straight chain or branched alkyl derivative substituted with 1–3 substituents selected from A, —T—C(O)R' or —$OPO_3H_2$.

A is selected from the groups:

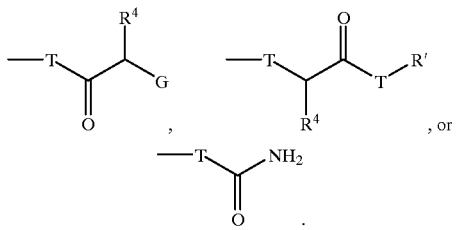

T is either O or NH.
G is either $NH_2$ or OH.
Z is either CH or N.
W is selected from H; $N(R^2)SO_2$—$N(R^2)_2$; $N(R^2)SO_2$—$N(R^2)(R^3)$; $N(R^2)C(O)$—$OR^2$; $N(R^2)C(O)$—$N(R^2)_2$; $N(R^2)C(O)$—$N(R^2)(R^3)$; $N(R^2)C(O)$—$R^2$; $N(R^2)_2$; C(O)—$R^2$; CH(OH)—$R^2$; C(O)—$N(R^2)_2$; C(O)—$OR^2$; or $(C_1$–$C_4)$ straight or branched alkyl optionally substituted with A, T—(CO)R', $N(R')_2$, OR', $CO_2R'$, $CON(R')_2$, $R^3$, or $SO_2N(R^2)_2$; or a 5–6 membered carbocyclic or heterocyclic ring system optionally substituted with $N(R')_2$, OR', $CO_2R'$, $CON(R')_2$, or $SO_2N(R^2)_2$.

R', $R^2$ and $R^3$ are defined as described above.

$R^4$ is $(C_1$–$C_4)$-alkyl optionally substituted with $N(R')_2$, OR', $CO_2R'$, $CON(R')_2$, or $SO_2N(R^2)_2$; a 5–6 membered carbocyclic or heterocyclic ring system optionally substituted with a $(C_1$–$C_4)$ branched or straight-chain alkyl group, $N(R')_2$, OR', $CO_2R'$, $CON(R')_2$, or $SO_2N(R^2)_2$; or a $(C_1$–$C_4)$-alkyl optionally substituted with the 5–6 membered carbocyclic or heterocyclic ring system optionally substituted with a $(C_1$–$C_4)$ branched or straight-chain alkyl group, $N(R')_2$, OR', $CO_2R'$, $CON(R')_2$, or $SO_2N(R^2)_2$.

In another embodiment, the invention provides pharmaceutical compositions comprising the p38 inhibitors of this invention. These compositions may be utilized in methods for treating or preventing a variety of disorders, such as cancer, inflammatory diseases, autoimmune diseases, destructive bone disorders, proliferative disorders, infectious diseases, viral diseases and neurodegenerative diseases. These compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. Each of these above-described methods is also part of the present invention.

DETAILED DESCRIPTION OF THE INVENTION

In order that the invention herein described may be more fully understood, the following detailed description is set forth. In the description, the following terms are employed:

The term "heterocyclyl" or "heterocycle" refers to a stable 5–7 membered monocyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom that results in the creation of a stable structure. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuranyl.

The term "pharmaceutically acceptable salts" refers to compounds according to the invention used in the form of salts derived from inorganic or organic acids and bases.

Included among acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate.

Salts derived from appropriate bases include alkali metal (e.g. sodium), alkaline earth metal (e.g., magnesium), ammonium and $NW_4^+$ (wherein W is $C_{1-4}$ alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$ alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulphonic acids such as methanesulphonic, ethanesulphonic, benzenesulphonic and p-toluenesulphonic acids and inorganic acids such as hydrochloric, sulphuric, phosphoric, sulphamic and pyrophosphoric acids.

For therapeutic use, salts of the compounds according to the invention will be pharmaceutically acceptable. However, salts of acids and bases that are not pharmaceutically acceptable may also find use, for example, in the preparation or purification of a pharmaceutically acceptable compound.

Preferred salts include salts formed from hydrochloric, sulfuric, acetic, succinic, citric and ascorbic acids.

The term "chemically feasible" refers to a connectivity of atoms such that the chemical valency of each atom is satisfied. For example, an oxygen atom with two bonds and a carbon atom with four bonds are chemically feasible.

The term "tautomerization" refers to the phenomenon wherein a proton of one atom of a molecule shifts to another atom. See, Jerry March, *Advanced Organic Chemistry: Reactions, Mechanisms and Structures,* Fourth Edition, John Wiley & Sons, pages 69–74 (1992). The term "tautomer" refers to the compounds produced by the proton shift. For example, when $R_1$ is —OH in a compound of formula I, the compound can exist as a tautomer as shown below:

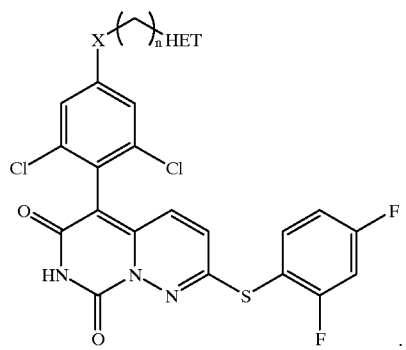

In one embodiment, the present invention provides inhibitors of p38 having the general formulae:

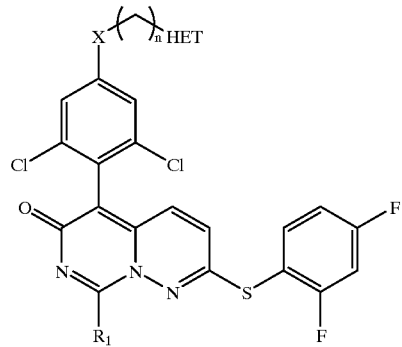

(Formula I)

and

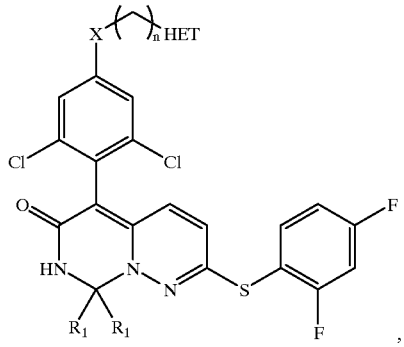

(Formula II)

pharmaceutically acceptable salts thereof.

HET is a 5–7-membered heterocycle with 1 to 4 N, S or O atoms, which heterocycle is substituted with 1 to 3 $C_1$–$C_4$ branched or straight chain alkyl groups. HET may optionally be substituted with halo, cyano, $N(R')_2$, OR', $CO_2R'$, $CON(R')_2$, and $SO_2N(R^2)_2$.

X is O or NR'.

n is 1 to 3.

R' is selected from hydrogen, ($C_1$–$C_3$)-alkyl, ($C_2$–$C_3$)-alkenyl or alkynyl, phenyl or phenyl substituted with 1 to 3 substituents independently selected from halo, methoxy, cyano, nitro, amino, hydroxy, methyl or ethyl; or a 5–6 membered heterocyclic ring system optionally substituted with 1 to 3 substituents independently selected from halo, methoxy, cyano, nitro, amino, hydroxy, methyl or ethyl.

$R_1$ is selected from hydrogen, ($C_1$–$C_3$)-alkyl, OH, or O—($C_1$–$C_3$)-alkyl.

$R^2$ is selected from hydrogen, ($C_1$–$C_3$)-alkyl, or ($C_1$–$C_3$)-alkenyl; each optionally substituted with —$N(R')_2$, —OR', SR', —C(O)—$N(R')_2$, —$S(O_2)$—$N(R')_2$, —C(O)—OR', or $R^3$.

$R^3$ is selected from 5–6 membered aromatic carbocyclic or heterocyclic ring systems.

It will be apparent to one of skill in the art that the compounds of the present invention may exist as tautomers. Such tautomers may be transient or isolatable as a stable product. These tautomers are envisioned within the scope of the invention. These compounds are also p38 inhibitors and fall within the scope of the present invention.

According to a preferred embodiment for Formulae I and II, $R_1$ is H, n is 1, and HET is an imidazole, triazole, thiazole, oxazole, pyridyl or pyrimidyl ring substituted with 1 to 3 $C_1$–$C_4$ branched or straight chain alkyl groups.

According to a more preferred embodiment for Formulae I and II, $R_1$ is H, n is 1 and HET is an imidazole or pyridyl ring substituted with a $C_1$–$C_3$ alkyl group.

Particularly preferred embodiments according to Formula I are

Compound 11

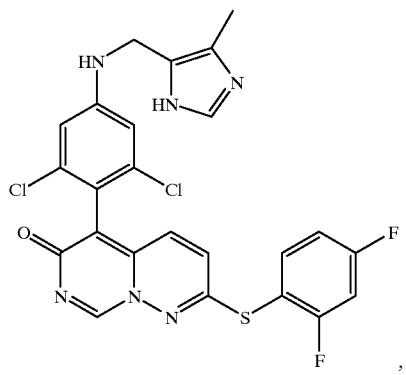

Compound 12

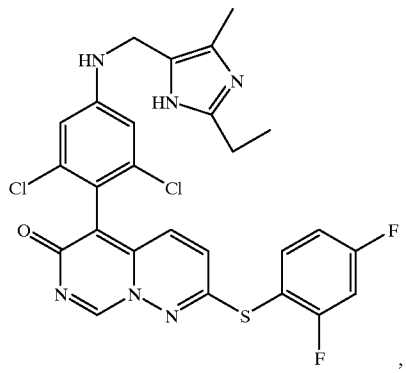

Compound 13

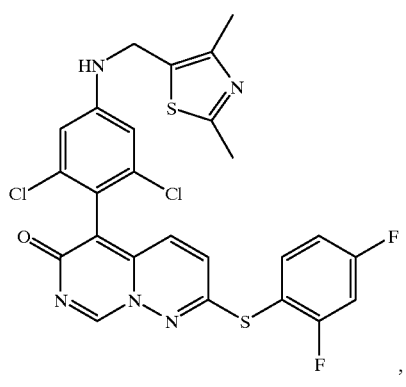

and

Compound 14

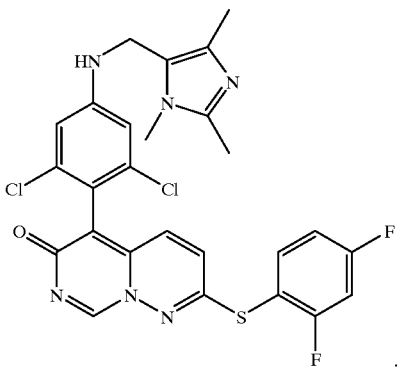

In another embodiment, p38-inhibitory compounds have the general formula:

(Formula III)

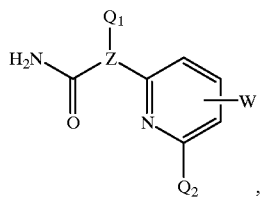

acceptable salts thereof.

Each of $Q_1$ and $Q_2$ are independently selected from 5–6 membered aromatic carbocyclic or heterocyclic ring systems, or 8–10 membered bicyclic ring systems comprising aromatic carbocyclic rings, aromatic heterocyclic rings or a combination of an aromatic carbocyclic ring and an aromatic heterocyclic ring.

The rings that make up $Q_1$ are optionally substituted with 1 to 4 substituents, each of which is independently selected from J; halo; $C_1$–$C_4$ alkyl optionally substituted with $NR'_2$, OR', $CO_2R'$ or $CONR'_2$; O—($C_1$–$C_4$)-alkyl optionally substituted with A, T—C(O)R', $OPO_3H_2$, $NR'_2$, $NR'_2$, OR', $CO_2R'$ or $CONR'_2$; $NR'_2$; $OCF_3$; $CF_3$; $NO_2$; $CO_2R'$; CONR'; SR'; $S(O_2)N(R')_2$; $SCF_3$; CN; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N=C-N(R')_2$.

The rings that make up $Q_2$ are substituted with J and optionally substituted with halo, $C_1$–$C_4$ straight chain or branched alkyl, hydroxy, methoxy, trifluoromethyl, trifluoromethoxy, cyano, or amino.

J is a $C_1$–$C_4$ straight chain or branched alkyl derivative substituted with 1–3 substituents selected from A, —T—C(O)R' or —$OPO_3H_2$.

A is selected from the groups:

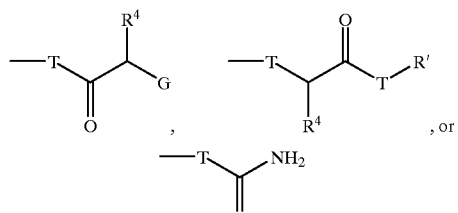

T is either O or NH.

G is either $NH_2$ or OH.

Z is either CH or N.

W is selected from H; $N(R^2)SO_2$—$N(R^2)_2$; $N(R^2)SO_2$—$N(R^2)(R^3)$; $N(R^2)C(O)$—$OR^2$; $N(R^2)C(O)$—$N(R^2)_2$; $N(R^2)C(O)$—$N(R^2)(R^3)$; $N(R^2)C(O)$—$R^2$; $N(R^2)_2$; $C(O)$—$R^2$; $CH(OH)$—$R^2$; $C(O)$—$N(R^2)_2$; $C(O)$—$OR^2$; or $(C_1-C_4)$ straight or branched alkyl optionally substituted with A, T—(CO)R', $N(R')_2$, OR', $CO_2R'$, $CON(R')_2$, $R^3$, or $SO_2N(R^2)_2$; or a 5–6 membered carbocyclic or heterocyclic ring system optionally substituted with $N(R')_2$, OR', $CO_2R'$, $CON(R')_2$, or $SO_2N(R^2)_2$.

R', $R^2$ and $R^3$ are definded as described above.

$R^4$ is $(C_1-C_4)$-alkyl optionally substituted with $N(R')_2$, OR', $CO_2R'$, $CON(R')_2$, or $SO_2N(R^2)_2$; a 5–6 membered carbocyclic or heterocyclic ring system optionally substituted with a $(C_1-C_4)$ branched or straight-chain alkyl group, $N(R')_2$, OR', $CO_2R'$, $CON(R')_2$, or $SO_2N(R^2)_2$; or a $(C_1-C_4)$-alkyl optionally substituted with the 5–6 membered carbocyclic or heterocyclic ring system optionally substituted with a $(C_1-C_4)$ branched or straight-chain alkyl group, $N(R')_2$, OR', $CO_2R'$, $CON(R')_2$, or $SO_2N(R^2)_2$.

According to a preferred embodiment for compounds of Formula III, $Q_1$ is selected from phenyl or pyridyl containing 1 to 3 substituents, wherein at least one of said substituents is in the ortho position and said substituents are independently selected from chloro, fluoro, bromo, —$CH_3$, —$OCH_3$, —OH, —$CF_3$, —$OCF_3$, —$O(CH_2)_2CH_3$, $NH_2$, 3,4-methylenedioxy, —$N(CH_3)_2$, —NH—$S(O)_2$-phenyl, —NH—C(O)O—$CH_2$—4-pyridine, —NH—$C(O)CH_2$-morpholine, —NH—$C(O)CH_2$—$N(CH_3)_2$, —NH—$C(O)CH_2$-piperazine, —NH—$C(O)CH_2$-pyrrolidine, —NH—C(O)C(O)-morpholine, —NH—C(O)C(O)-piperazine, —NH—C(O)C(O)-pyrrolidine, —O—$C(O)CH_2$—$N(CH_3)_2$, or —O—$(CH_2)_2$—$N(CH_3)_2$.

Even more preferred are phenyl or pyridyl containing at least 2 of the above-indicated substituents both being in the ortho position.

Some specific examples of preferred $Q_1$ are:

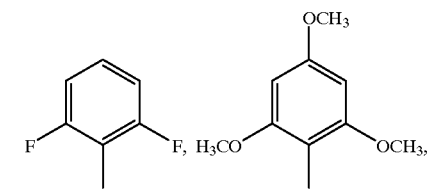

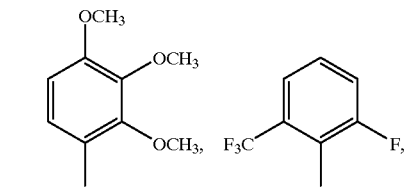

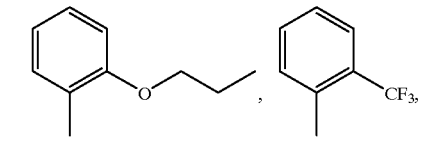

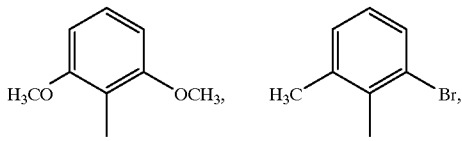

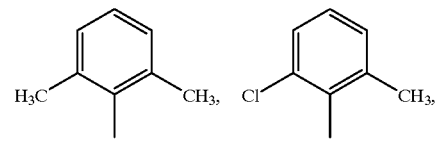

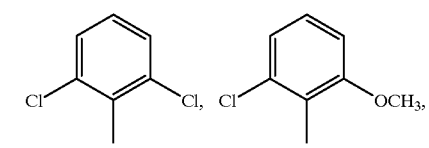

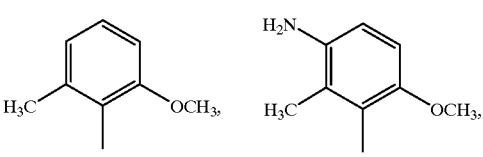

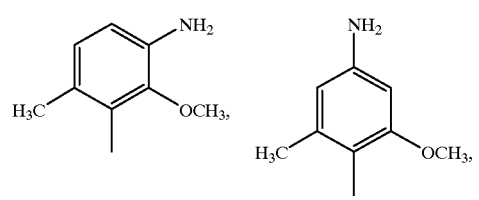

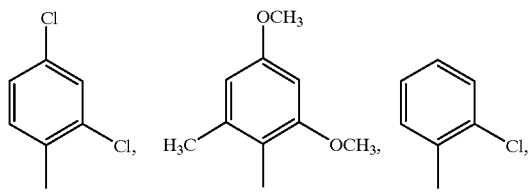

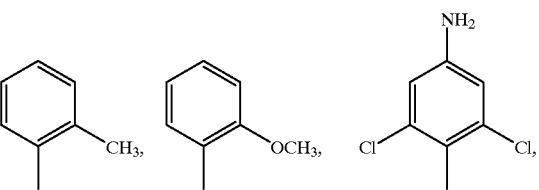

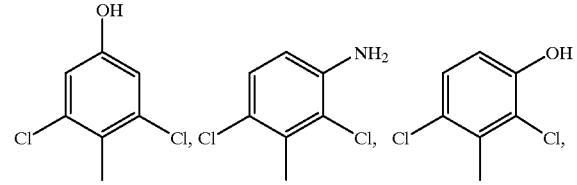

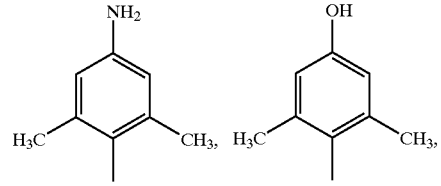

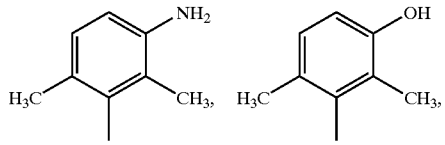

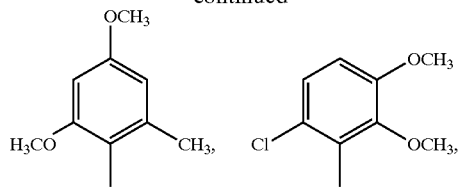
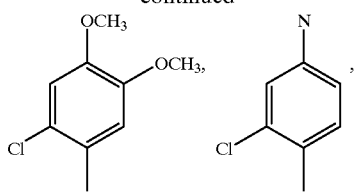
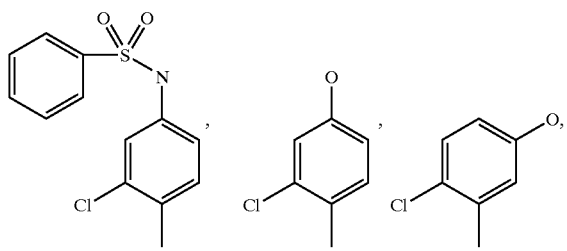
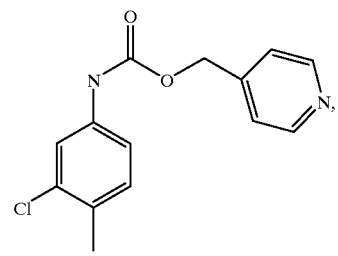
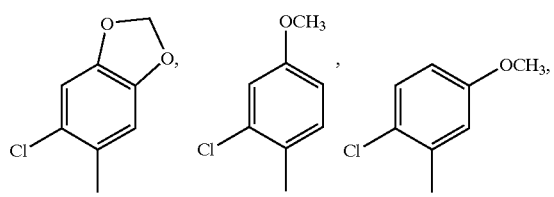
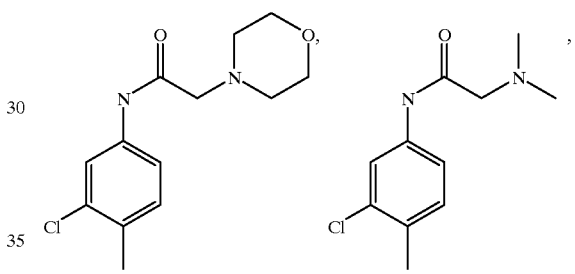
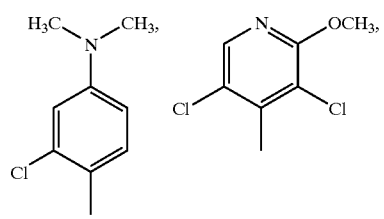
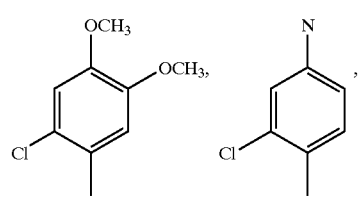
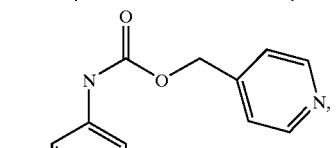
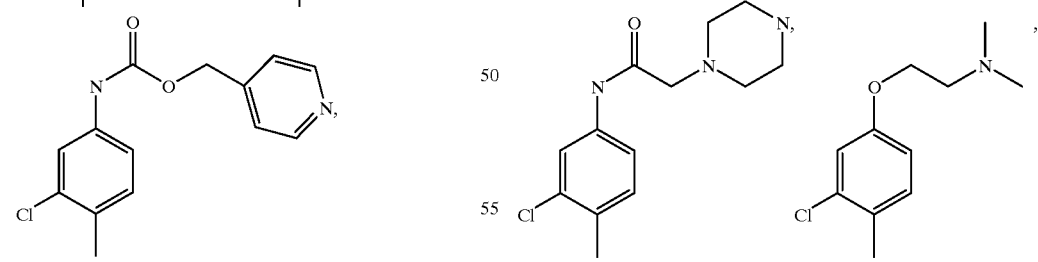
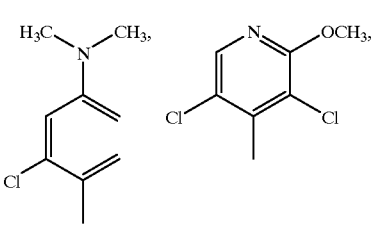
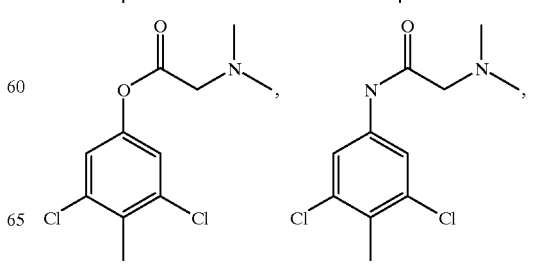

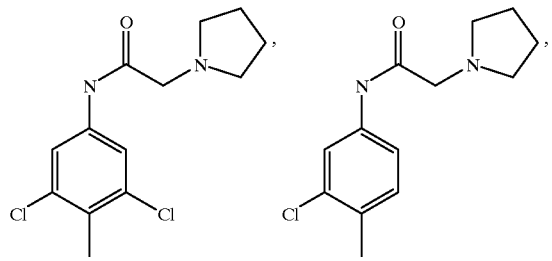

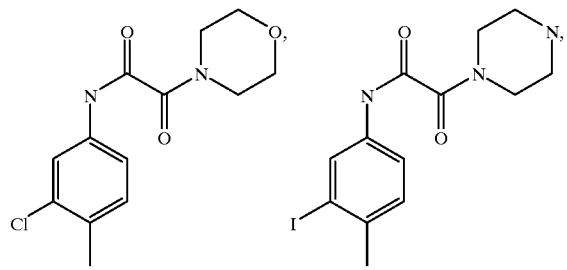

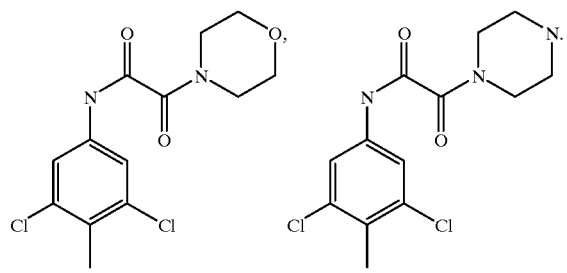

Most preferably, Q₁ is selected from 2-fluoro-6-trifluoromethylphenyl, 2,6-difluorophenyl, 2,6-dichlorophenyl, 2-chloro-4-hydroxyphenyl, 2-chloro-4-aminophenyl, 2,6-dichloro-4-aminophenyl, 2,6-dichloro-3-aminophenyl, 2,6-dimethyl-4-hydroxyphenyl, 2-methoxy-3,5-dichloro-4-pyrifyl, 2-chloro-4,5 methylenedioxy phenyl, or 2-chloro-4-(N-2-morpholino-acetamido)phenyl.

According to a preferred embodiment, Q₂ is phenyl or pyridyl, wherein the phenyl or pyridyl contains the substituent J and 0 to 3 other substituents, wherein each of these other substituents is independently selected from chloro, fluoro, bromo, methyl, ethyl, isopropyl, —OCH₃, —OH, —NH₂, —CF₃, —OCF₃, —SCH₃, —OCH₃, —C(O) OH, —C(O)OCH₃, —CH₂NH₂, —N(CH₃)₂, —CH₂-pyrrolidine and —CH₂OH.

Particularly preferred embodiments according to Formula III are

Compound 15

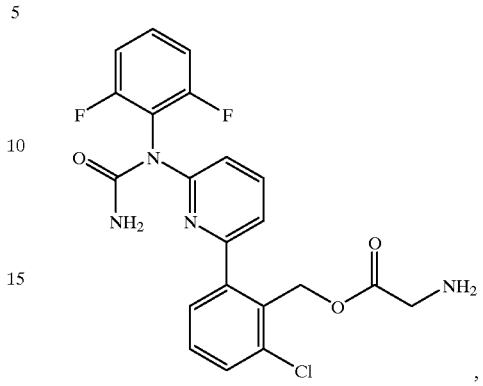

Compound 16

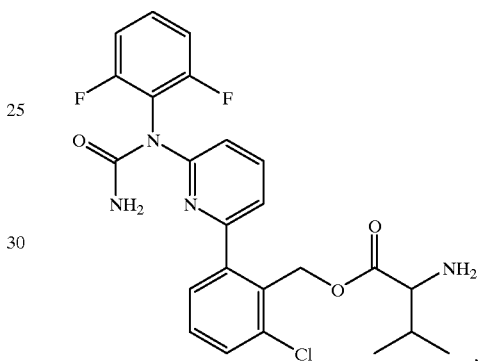

Compound 17

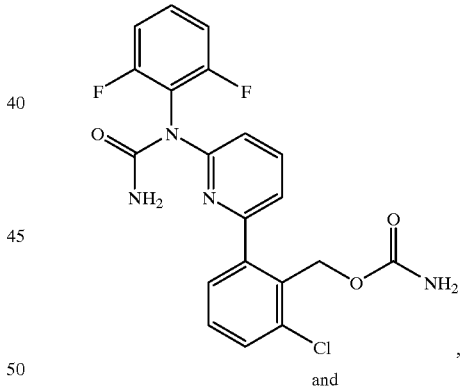

and

Compound 18

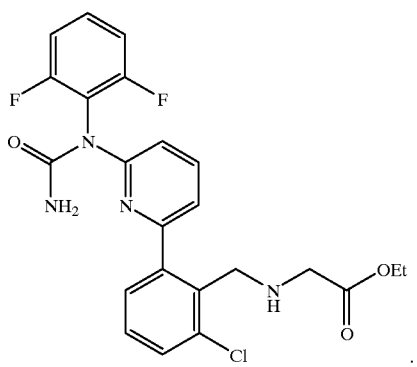

It will be apparent to one of skill in the art that the compounds of the present invention may exist as tautomers. Such tautomers may be transient or isolatable as a stable product. These tautomers are envisioned within the scope of the invention. These compounds are also p38 inhibitors and fall within the scope of the present invention.

It will also be apparent to one of skill in the art that when Z is CH in compounds of Formula III, a chiral compound is formed. In this case, both enantiomers are envisioned within the scope of the invention.

According to another embodiment, the present invention provides methods of producing the above-identified inhibitors of p38. A method of producing compound 11 is provided in Example 1.

The activity of the p38 inhibitors of this invention may be assayed in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands.

Cell culture assays of the inhibitory effect of the compounds of this invention may be used to determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention is the suppression of hind paw edema in rats with *Mycobacterium butyricum*-induced adjuvant arthritis. This is described in J. C. Boehm et al., *J. Med. Chem.*, 39, pp. 3929–37 (1996), the disclosure of which is herein incorporated by reference. The p38 inhibitors of this invention may also be assayed in animal models of arthritis, bone resorption, endotoxin shock and immune function, as described in A. M. Badger et al., *J. Pharmacol. Experimental Therapeutics*, 279, pp. 1453–61 (1996), the disclosure of which is herein incorporated by reference.

The p38 inhibitors or pharmaceutical salts thereof may be formulated into pharmaceutical compositions for administration to animals or humans. These pharmaceutical compositions, which comprise and amount of p38 inhibitor effective to treat or prevent a p38-mediated condition and a pharmaceutically acceptable carrier, are another embodiment of the present invention.

The term "p38-mediated condition", as used herein means any disease or other deleterious condition in which p38 is known to play a role. This includes conditions caused by IL-1, TNF, IL-6 or IL-8 overproduction. Such conditions include, without limitation, inflammatory diseases, autoimmune diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Angiogenic disorders which may be treated or prevented include solid tumors, ocular neovasculization, infantile haemangiomas.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, cerebral ischemias or neurodegenerative disease caused by traumatic injury.

"p38-mediated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors in this invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, pain caused by cancer, dental pain and arthritis pain.

The diseases that may be treated or prevented by the p38 inhibitors of this invention may also be conveniently grouped by the cytokine (IL-1, TNF, IL-6, IL-8) that is believed to be responsible for the disease.

Thus, IL-1-mediated diseases or conditions include rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic B-cell disease and Alzheimer's disease.

TNF-mediated diseases or conditions include rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated diseases or conditions include diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this invention may be used topically to treat or prevent conditions caused or exacerbated by IL-1 or TNF. Such conditions include inflamed joints, eczema, psoriasis, inflammatory skin conditions such as sunburn, inflammatory eye conditions such as conjunctivitis, pyresis, pain and other conditions associated with inflammation.

In addition to the compounds of this invention, pharmaceutically acceptable salts of the compounds of this invention may also be employed in compositions to treat or prevent the above-identified disorders.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N—($C_{1-4}$ alkyl)4+ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of p38 inhibitor that may be combined with the carrier materials to produce a single dosage form will vary depending upon the host treated, the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, angiogenic disorders, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition may be administered together with the inhibitors of this invention. For example, chemotherapeutic agents or other anti-proliferative agents may be combined with the p38 inhibitors of this invention to treat proliferative diseases.

Those additional agents may be administered separately, as part of a multiple dosage regimen, from the p38 inhibitor-containing composition. Alternatively, those agents may be part of a single dosage form, mixed together with the p38 inhibitor in a single composition.

In order that the invention described herein may be more fully understood, the following examples are set forth. It should be understood that these examples are for illustrative purposes only and are not to be construed as limiting this invention in any manner.

EXAMPLE 1

Preparation of Compound 11

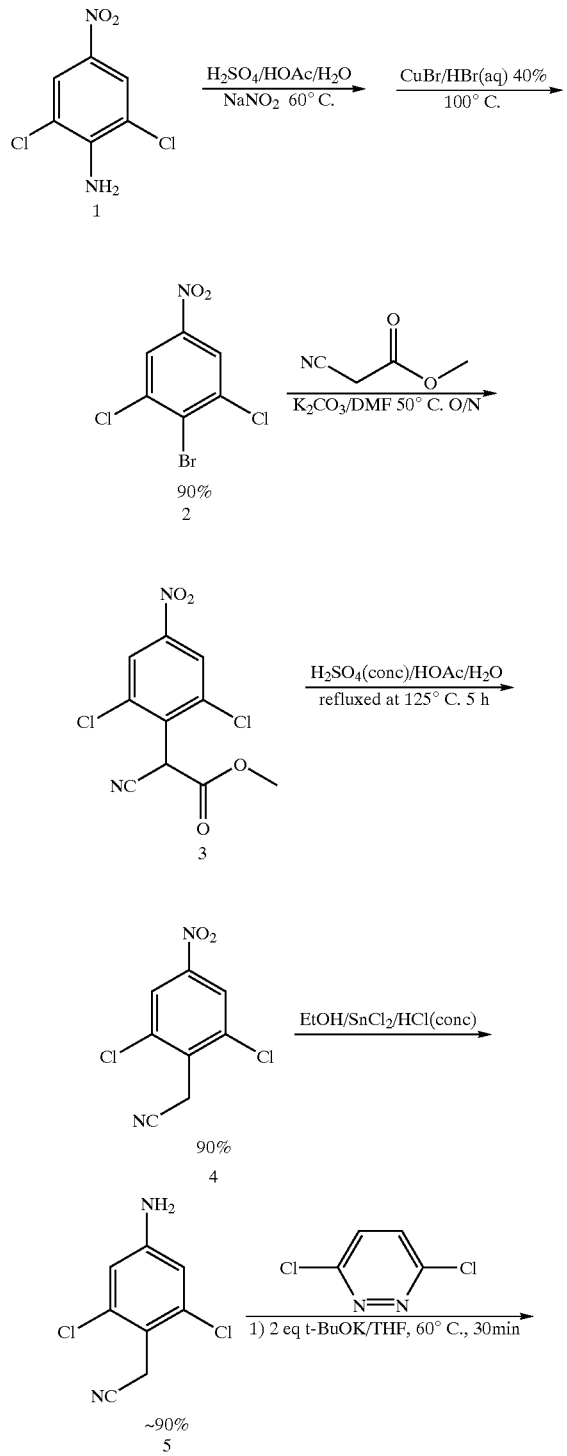

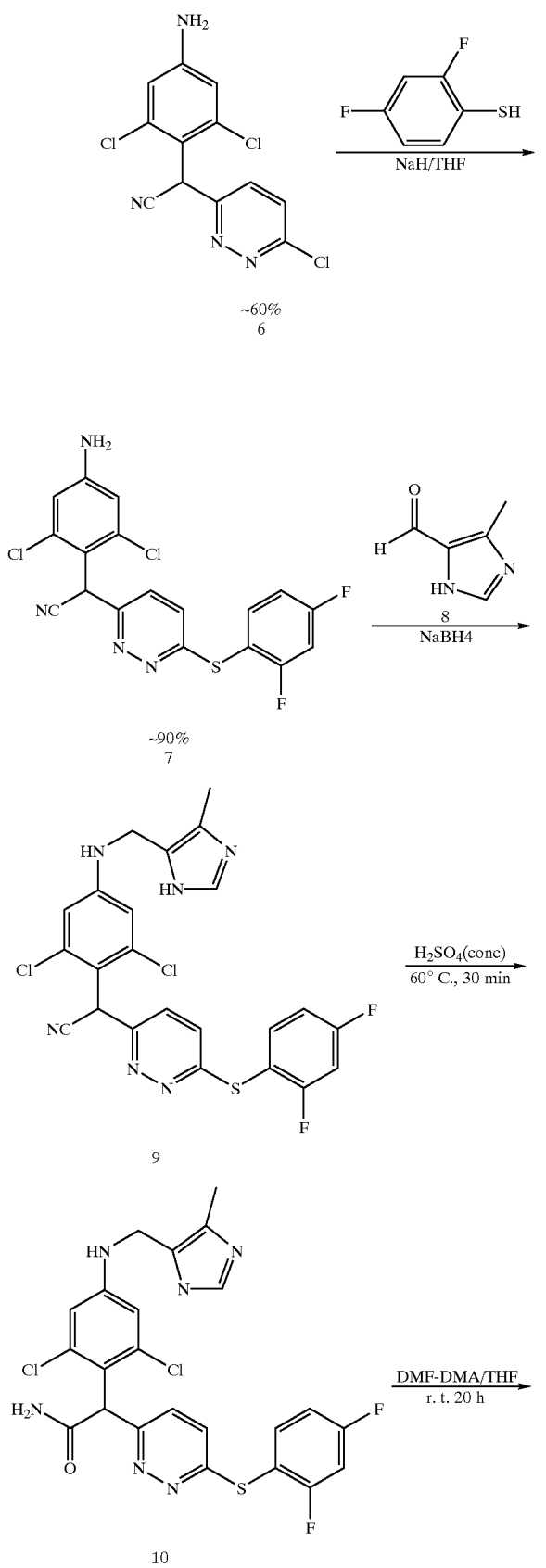

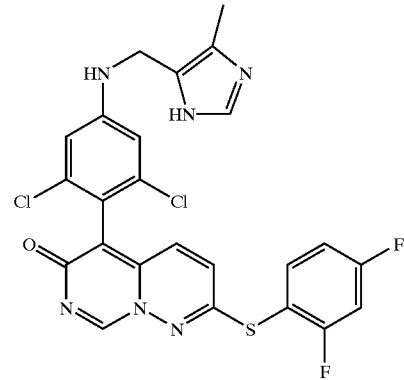

Compound 1 was dissolved in a 1:20 ratio in a solution of concentrated sulfuric acid and glacial acetic acid (1:4). Aqueous NaNO$_2$ was added dropwise to the solution over two hours (h). The reaction mixture was stirred at 60° C. for one hour. This solution was transferred to one equivalent of CuBr and three equivalents of HBr (stock concentration of HBr was 48%) at 100° C. over one hour. The reaction mixture was stirred at 100° C. for one hour. The reaction mixture was poured into ice. Compound 2 was precipitated, filtered and further purified by chromatography. The yield of compound 2 was 90%.

One equivalent of compound 2 and one equivalent of methyl cyanoacetate were dissoved in dimethyl formamide (DMF). Two equivalents of K$_2$CO$_3$ were added to the DMF solution at 50° C. The reaction mixture was stirred at 50° C. overnight. The reaction mixture was poured into a HCl/crushed-ice bath. Compound 3 was precipitated, filtered and directly used for next step. The yield of compound 3 was 90%.

Compound 3 was dissolved in a solution of 5% concentrated sulfuric acid, 47.5% acetic acid and 47.5% water. The reaction mixture was stirred at 125° C. for five hours. The reaction mixture was poured into an excess of crushed ice. Compound 4 was precipitated, filtered and directly used for next step without further purification. The yield of compound 4 was 90%.

Compound 4 was suspended in ethyl alcohol. Concentrated HCl containing 4.5 equivalent of SnCl$_2$ was added at 75° C. The reaction mixture was refluxed for 30 min. at 75° C. Thin layer chromatography (TLC) indicated the reaction was completed. The reaction solution was cooled to room temperature. The precipitate was filtered, dissolved in ethyl acetate, and the organic phase was washed with saturated K$_2$CO$_3$ and NaCl, then was dried with MgSO$_4$. The solvent was removed under reduced pressure. Compound 5 was obtained pure at a yield of 90%.

One equivalent of compound 5 and one equivalent of 3,6-dichloropyridazine were dissolved in tetrahydrofuran (THF) at 60° C. Two equivalents of potassium t-butyl hydroxide were added. The reaction mixture was stirred at 60° C. for one hour. Saturated NaCl and ethyl acetate were added to the reaction mixture. The pH of the aqueous phase was adjusted to 7 with HCl and extracted with ethyl acetate. The organic phase was washed with saturated NaCl two times and dried with $MgSO_4$. The solvent was removed under reduced pressure. Compound 6 was purified by chromatography at a yield of 60%.

A THF solution of 2,4-difluorothiophenol at 0–5° C. was added to NaH. The suspension was stirred at 0–5° C. until no more bubbles were released and the reaction mixture became a clear solution. The solution was then warmed to 60° C. Compound 6 at 60° C. was added to this solution. The reaction was refluxed until TLC indicated compound 6 was consumed. Saturated NaCl and ethyl acetate were added to the reaction mixture. The organic phase was washed with saturated NaCl two times and dried with $MgSO_4$. The solvent was removed under reduced pressure. Compound 7 was purified by chromatography at a yield of 90%.

A toluene solution of compound 7 and aldehyde 8 was refluxed for 24 h. The imine formed was purified by chromatography, dissolved in anhydrous methyl alcohol, and reduced to amine 9 with $NaBH_4$ in the presence of catalytic amount of acetic acid. The reaction was quenched with water and extracted with ethyl acetate. The organic layer was removed under vacuum and the crude amine was stirred with concentrated sulfuric acid solution at 100° C. for 30 min. The amide 10 was precipitated out from a NaCl/crushed-ice bath, filtered and directly used in the ring closure step. Amide 10 was dissolved in THF. Excess DMF-DMA was added to the solution. The reaction solution was stirred at 70° C. for one to two hours. The product 11 was purified by crystallization from ethyl acetate.

EXAMPLE 2

Cloning of p38 Kinase in Insect Cells

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET-15b vector (Novagen). The baculovirus transfer vector, pVL-(His)6-p38 was constructed by subcloning a XbaI-BamHI fragment of pET15b-(His)6-p38 into the complementary sites in plasmid pVL1392 (Pharmingen).

The plasmid pVL-(His)6-p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of *Spodoptera frugiperda* (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of *Autographa califonica* nuclear polyhedrosis virus (Pharmingen) and transfer vector pVL-(His)6-p38 using Lipofectin (Invitrogen). The individual recombinant baculovirus clones were purified by plaque assay using 1% low melting agarose.

EXAMPLE 3

Expression and Purification of Recombinant p38 Kinase

Trichoplusia ni (Tn-368) High-Five™ cells (Invitrogen) were grown in suspension in Excel-405 protein free medium (JRH Bioscience) in a shaker flask at 27° C. Cells at a density of $1.5 \times 10^6$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the $(His)_6$-tagged p38 was thawed in 5 volumes of Buffer A (50 mM $NaH_2PO_4$ pH 8.0, 200 mM NaCl, 2 mM β-Mercaptoethanol, 10% Glycerol and 0.2 mM PMSF). After mechanical disruption of the cells in a microfluidizer, the lysate was centrifuged at 30,000×g for 30 minutes. The supernatant was incubated batchwise for 3–5 hours at 4° C. with Talon™ (Clontech) metal affinity resin at a ratio of 1 ml of resin per 2–4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidazole.

The $(His)_6$-p38 was eluted with Buffer A+100 mM imidazole and subsequently dialyzed overnight at 4° C. against 2 liters of Buffer B, (50 mM HEPES, pH 7.5, 25 mM β-glycerophosphate, 5% glycerol, 2 mM DTT). The $His_6$ tag was removed by addition of at 1.5 units thrombin (Calbiochem) per mg of p38 and incubation at 20° C. for 2–3 hours. The thrombin was quenched by addition of 0.2 mM PMSF and then the entire sample was loaded onto a 2 ml benzamidine agarose (American International Chemical) column.

The flow through fraction was directly loaded onto a 2.6×5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3–4 ml and applied to a 2.6×100 cm Sephacryl S-100HR (Pharmacia) column. The protein was eluted at a flow rate of 35 ml/hr. The main peak was pooled, adjusted to 20 mM DTT, concentrated to 10–80 mgs/ml and frozen in aliquots at −70° C. or used immediately.

EXAMPLE 4

Activation of p38 p38 was activated by combining 0.5 mg/ml p38 with 0.005 mg/ml DD-double mutant MKK6 in Buffer B+10 mM $MgCl_2$, 2 mM ATP, 0.2 mM $Na_2VO_4$ for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM $Na_2VO_4$ to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+ 1.1MK2HPO4. The protein was eluted with a 20 column volume linear gradient to Buffer D+50 mM K2HPO4. The double phosphorylated p38 eluted as the main peak and was pooled for dialysis against Buffer B+0.2 mM Na2VO4. The activated p38 was stored at −70° C.

EXAMPLE 5

P38 Inhibition Assays

A. Inhibition of Phosphorylation of EGF Receptor Peptide

This assay is carried out in the presence of 10 mM MgCl2, 25 mM β-glycerophosphate, 10% glycerol and 100 mM HEPES buffer at pH 7.6. For a typical $IC_{50}$ determination, a stock solution is prepared containing all of the above components and activated p38 (5 nM). The stock solution is aliquotted into vials. A fixed volume of DMSO or inhibitor in DMSO (final concentration of DMSO in reaction is 5%) is introduced to each vial, mixed and incubated for 15 minutes at room temperature. EGF receptor peptide, KRELVEPLTPSGEAPNQALLR, a phosphoryl acceptor in p38-catalyzed kinase reaction, is added to each vial to a final concentration of 200 μM. The kinase reaction is initiated with ATP (100 μM) and the vials are incubated at 30° C. After 30 minutes, the reactions are quenched with equal volume of 10% trifluoroacetic acid (TFA).

The phosphorylated peptide is quantified by HPLC analysis. Separation of phosphorylated peptide from the unphosphorylated peptide is achieved on a reverse phase column (Deltapak, 5 um, C18 100D, part no. 011795) with a binary gradient of water and actecnitrile, each containing 0.1% TFA. $IC_{50}$ (concentration of inhibitor yielding 50% inhibition) is determined by plotting the % activity remaining against inhibitor concentration.

B. Inhibition of ATPase Activity

This assay is carried out in the presence of 10 mM MgCl2, 25 mM β-glycerophosphate, 10% glycerol and 100 mM HEPES buffer at pH 7.6. For a typical Ki determination, the Km for ATP in the ATPase activity of activated p38 reaction is determined in the absence of inhibitor and in the presence of two concentrations of inhibitor. Ki is determined from the rate data as a function of inhibitor and ATP concentrations. A stock solution is prepared containing all of the above components and activated p38 (60 nM). The stock solution is aliquoted into vials. A fixed volume of DMSO or inhibitor in DMSO (final concentration of DMSO in reaction is 2.5%) is introduced to each vial, mixed and incubated for 15 minutes at room temperature. The reaction is initiated by adding various concentrations of ATP and then incubated at 30° C. After 30 minutes, the reactions are quenched with 50 μl of EDTA (0.1 M, final concentration), pH 8.0. The product of p38 ATPase activity, ADP, is quantified by HPLC analysis.

Separation of ADP from ATP is achieved on a reversed phase column (Supelcosil, LC-18, 3 μm, part no. 5–8985) using a binary solvent gradient of following composition: Solvent A–0.1 M phosphate buffer containing 8 mM tetrabutylammonium hydrogen sulfate (Sigma Chemical Co., catalogue no. T-7158), Solvent B–Solvent A with 30% methanol.

C. Inhibition of IL-1, TNF, IL-6 and IL-8 Production in LPS-Stimulated PBMCs

Inhibitors are serially diluted in DMSO from a 20 mM stock. At least 6 serial dilutions are prepared. Then 4× inhibitor stocks are prepared by adding 4 μl of an inhibitor dilution to 1 ml of RPMI1640 medium/10% fetal bovine serum. The 4× inhibitor stocks contained inhibitor at concentrations of 80 μM, 32 μM, 12.8 μM, 5.12 μM, 2.048 μM, 0.819 μM, 0.328 μM, 0.131 μM, 0.052 μM, 0.021 μM etc. The 4× inhibitor stocks are pre-warmed at 37° C. until use.

Fresh human blood buffy cells are separated from other cells in a Vacutainer CPT from Becton & Dickinson (containing 4 ml blood and enough DPBS without $Mg^{2+}$/$Ca^{2+}$ to fill the tube) by centrifugation at 1500×g for 15 min. Peripheral blood mononuclear cells (PBMCs), which are located on top of the gradient in the Vacutainer, are removed and washed twice with RPMI1640 medium/10% fetal bovine serum. PBMCs are collected by centrifugation at 500×g for 10 min. The total cell number is determined using a Neubauer Cell Chamber and the cells are adjusted to a concentration of $4.8 \times 10^6$ cells/ml in cell culture medium (RPMI1640 supplemented with 10% fetal bovine serum).

Alternatively, whole blood containing an anti-coagulant is used directly in the assay.

100 μl of cell suspension or whole blood is placed in each well of a 96-well cell culture plate. Then, 50 μl of the 4× inhibitor stock to the cells is added. Finally, 50 μl of a lipopolysaccharide (LPS) working stock solution (16 ng/ml in cell culture medium) is added to give a final concentration of 4 ng/ml LPS in the assay. The total assay volume of the vehicle control is also adjusted to 200 μl by adding 50 μl cell culture medium. The PBMC cells or whole blood are then incubated overnight (for 12–15 hours) at 37° C./5% CO2 in a humidified atmosphere.

The next day the cells are mixed on a shaker for 3–5 minutes before centrifugation at 500×g for 5 minutes. Cell culture supernatants are harvested and analyzed by ELISA for levels of IL-1b (R & D Systems, Quantikine kits, #DBL50), TNF-α (BioSource, #KHC3012), IL-6 (Endogen, #EH2-IL6) and IL-8 (Endogen, #EH2-IL8) according to the instructions of the manufacturer. The ELISA data are used to generate dose-response curves from which IC50 values are derived.

p38 inhibitors of this invention will inhibit phosphorylation of EGF receptor peptide, and the production of IL-1, TNF and IL-6, as well as IL-8 in LPS-stimulated PBMCs or in whole blood.

D. Inhibition of IL-6 and IL-8 Production in IL-1-Stimulated PBMCs

This assay is carried out on PBMCs exactly the same as above except that 50 μl of an IL-1b working stock solution (2 ng/ml in cell culture medium) is added to the assay instead of the (LPS) working stock solution.

Cell culture supernatants are harvested as described above and analyzed by ELISA for levels of IL-6 (Endogen, #EH2-IL6) and IL-8 (Endogen, #EH2-IL8) according to the instructions of the manufacturer. The ELISA data are used to generate dose-response curves from which IC50 values are derived.

E. Inhibition of LPS-Induced Prostaglandin Endoperoxide Synthase-2 (PGHS-2, or COX-2) Induction In PBMCs Human peripheral mononuclear cells (PBMCs) are isolated from fresh human blood buffy coats by centrifugation in a Vacutainer CPT (Becton & Dickinson). $15 \times 10^6$ cells are seeded in a 6-well tissue culture dish containing RPMI 1640 supplemented with 10% fetal bovine serum, 50U/ml penicillin, 50 μg/ml streptomycin, and 2 mM L-glutamine. An inhibitor of the instant invention is added at 0.2, 2.0 and 20 μM final concentrations in DMSO. Then, LPS is added at a final concentration of 4 ng/ml to induce enzyme expression. The final culture volume is 10 ml/well.

After overnight incubation at 37° C., 5% CO2, the cells are harvested by scraping and subsequent centrifugation, then the supernatant is removed, and the cells are washed twice in ice-cold DPBS (Dulbecco's phosphate buffered saline, BioWhittaker). The cells are lysed on ice for 10 min in 50 μl cold lysis buffer (20 mM Tris-HCl, pH 7.2, 150 mM NaCl, 1% Triton-X-100, 1% deoxycholic acid, 0.1% SDS, 1 mM EDTA, 2% aprotinin (Sigma), 10 μg/ml pepstatin, 10 μg/ml leupeptin, 2 mM PMSF, 1 mM benzamidine, 1 mM DTT) containing 1 μl Benzonase (DNAse from Merck). The protein concentration of each sample is determined using the BCA assay (Pierce) and bovine serum albumin as a standard. Then the protein concentration of each sample is adjusted to 1 mg/ml with cold lysis buffer. To 100 μl lysate an equal volume of 2×SDS PAGE loading buffer is added and the sample is boiled for 5 min. Proteins (30 μg/lane) are size-fractionated on 4–20% SDS PAGE gradient gels (Novex) and subsequently transferred onto nitrocellulose membrane by electrophoretic means for 2 hours at 100 mA in Towbin transfer buffer (25 mM Tris, 192 mM glycine) containing 20% methanol. The membrane is pretreated for 1 hour at room temperature with blocking buffer (5% non-fat dry milk in DPBS supplemented with 0.1% Tween-20) and washed 3 times in DPBS/0.1% Tween-20. The membrane is incubated overnight at 4° C. with a 1:250 dilution of monoclonal anti-COX-2 antibody (Transduction Laboratories) in blocking buffer. After 3 washes in DPBS/0.1% Tween-20, the membrane is incubated with a 1:1000 dilution of horseradish peroxidase-conjugated sheep antiserum to mouse Ig (Amersham) in blocking buffer for 1 h at room temperature. Then the membrane is washed again 3 times in DPBS/0.1% Tween-20 and an ECL detection system (SuperSignal™ CL-HRP Substrate System, Pierce) is used to determine the levels of expression of COX-2.

While we have hereinbefore presented a number of embodiments of this invention, it is apparent that our basic construction can be altered to provide other embodiments which utilize the methods of this invention.

We claim:

1. A compound having the formula:

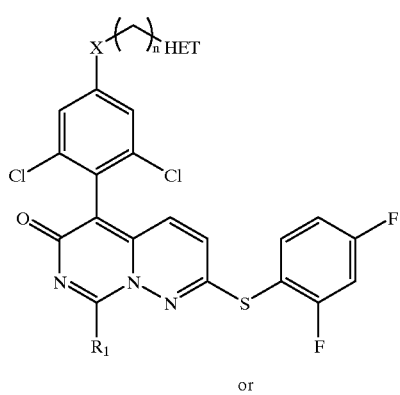

I or

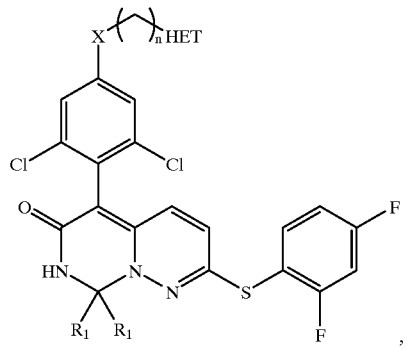

II or tautomers thereof or pharmaceutically acceptable salts thereof; wherein:

HET is a 5–7-membered heterocycle with 1 to 4 ring N, S or O atoms, which heterocycle is substituted with 1 to 3 $C_1$–$C_4$ branched or straight chain alkyl groups; wherein HET is optionally substituted with halo, cyano, N(R')$_2$, OR'CO$_2$R', CON(R')$_2$, or SO$_2$N(R$^2$)$_2$;

X is O or NR';

n is 1 to 3;

each R' is independently selected from hydrogen, ($C_1$–$C_3$)-alkyl, ($C_2$–$C_3$)-alkenyl or alkynyl, phenyl or phenyl substituted with 1 to 3 substituents independently selected from halo, methoxy, cyano, nitro, amino, hydroxy, methyl or ethyl; or a 5–6 membered heterocyclic ring system optionally substituted with 1 to 3 substituents independently selected from halo, methoxy, cyano, nitro, amino, hydroxy, methyl, or ethyl;

$R_1$ is selected from hydrogen, ($C_1$–$C_3$)-alkyl, OH, or O—($C_1$–$C_3$)-alkyl;

$R^2$ is selected from hydrogen, ($C_1$–$C_3$)-alkyl, or ($C_2$–$C_3$)-alkenyl; each optionally substituted with —N(R')$_2$, —OR', SR', —C(O)—N(R')$_2$, —S(O$_2$)—N(R')$_2$, —C(O)—OR', or R$^3$; and $R^3$ is selected from 5–6 membered aromatic carbocyclic or heterocyclic ring systems.

2. The compound according to claim 1, wherein $R_1$ is hydrogen.

3. The compound according to claim 1, wherein n is 1.

4. The compound according to claim 1, wherein HET is an imidazole, triazole, thiazole, oxazole, pyridyl or pyrimidyl ring substituted with 1 to 3 $C_1$–$C_4$ branched or straight chain alkyl groups.

5. The compound according to claim 1, wherein $R_1$ is hydrogen, n is 1, and HET is an imidazole, triazole, thiazole, oxazole, pyridyl or pyrimidyl ring substituted with 1 to 3 $C_1$–$C_4$ branched or straight chain alkyl groups.

6. The compound according to claim 5, wherein $R_1$ is H, n is 1 and HET is an imidazole or pyridyl ring substituted with a $C_1$–$C_3$ alkyl group.

7. The compound according to claim 1, wherein said compound is

Compound 11

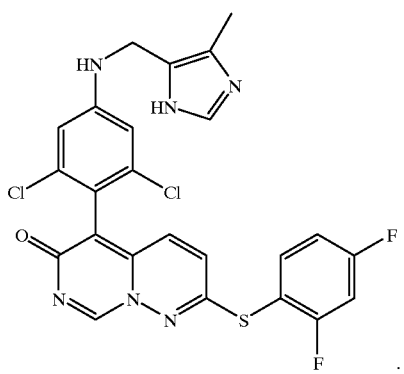

8. The compound according to claim 1, wherein said compound is

Compound 12

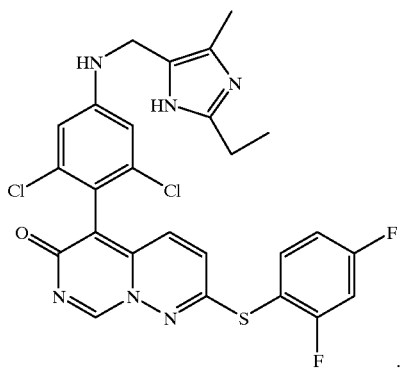

9. The compound according to claim 1, wherein said compound is

Compound 13

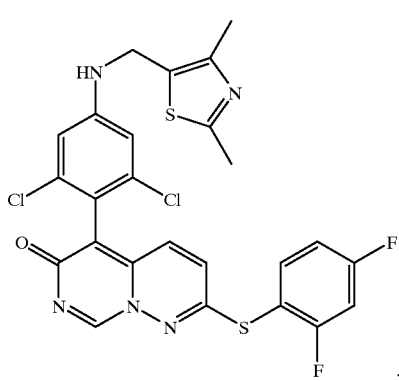

10. The compound according to claim 1, wherein said compound is

Compound 14

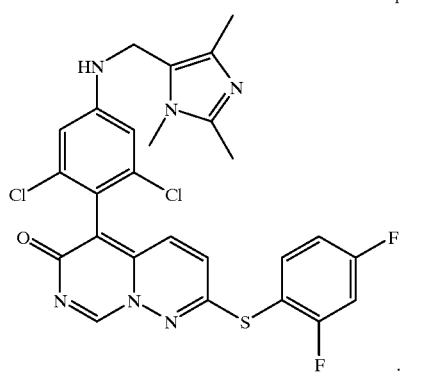

Compound 14

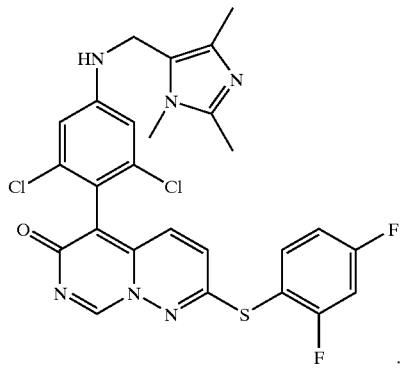

11. A composition comprising a compound according to claim 1 and a pharmaceutically acceptable carrier.

12. A method of treating inflammatory diseases, destructive bone disorders, reperfusion/ischemia in stroke, myocardial ischemia, renal ischemia, cardiac hypertrophy, rheumatoid arthritis, inflammatory bowel disease, ulcerative colitis, or Crohn's disease in a patient, said method comprising administering to said patient a composition according to claim 11 in an amount effective to inhibit p38.

13. The method according to claim 12, wherein said method is used to treat an inflammatory disease selected from acute pancreatitis, chronic pancreatitis, asthma, allergies, or adult respiratory distress syndrome.

14. The method according to claim 12, wherein said method is used to treat rheumatoid arthritis, inflammatory bowel disease, ulcerative colitis, or Crohn's disease.

15. The method according to claim 12, wherein said method is used to treat a destructive bone disorders selected from osteoarthritis, osteoporosis or multiple myeloma-related bone disorder.

16. The method according to claim 12, wherein said method is used to treat ischemia/reperfusion in stroke or myocardial ischemia, or renal ischemia.

* * * * *